US008334383B2

(12) United States Patent
Duran et al.

(10) Patent No.: US 8,334,383 B2
(45) Date of Patent: Dec. 18, 2012

(54) REGIOSELECTIVE PREPARATION OF SUBSTITUTED PYRIMIDINES

(75) Inventors: Adil Duran, Biberach (DE); Stefan Goepper, Biberach (DE); Joerg Halmer, Biberach (DE); Michael Konrad, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/933,174

(22) PCT Filed: Mar. 19, 2009

(86) PCT No.: PCT/EP2009/053271
§ 371 (c)(1),
(2), (4) Date: Oct. 25, 2010

(87) PCT Pub. No.: WO2009/115587
PCT Pub. Date: Sep. 24, 2009

(65) Prior Publication Data
US 2011/0077403 A1 Mar. 31, 2011

(30) Foreign Application Priority Data
Mar. 20, 2008 (EP) ..................................... 08153122

(51) Int. Cl.
*C07D 239/02* (2006.01)
(52) U.S. Cl. ........................................ 544/330; 544/332
(58) Field of Classification Search .................. 544/332, 544/330
See application file for complete search history.

(56) References Cited

U.S. PATENT DOCUMENTS 7,122,670 B2 * 10/2006 Kath et al. ..................... 544/330
7,928,109 B2 * 4/2011 Luzzio et al. ............. 514/255.05
2011/0060141 A1 * 3/2011 Linz et al. ..................... 544/310
2011/0190499 A1 8/2011 Linz et al.
2012/0172596 A1 7/2012 Linz et al.

FOREIGN PATENT DOCUMENTS

| JP | 62000062 | | 1/1987 |
| WO | 2005023780 A1 | | 3/2005 |
| WO | WO 2006117560 A1 | * | 11/2006 |
| WO | 2008071587 A2 | | 6/2008 |
| WO | 2009115583 A1 | | 9/2009 |
| WO | 2011018517 A1 | | 2/2011 |
| WO | 2011018518 A1 | | 2/2011 |

OTHER PUBLICATIONS

J. March, Advanced Organic Chemistry Reactions, Mechanisms and Structure 248-272 (4th ed., 1992).*
J. March, Advanced Organic Chemistry Reactions, Mechanisms and Structure 205, 352-357, 652-653 (4th ed., 1992).*
The Condensed Chemical Dictionary 822 (Gessner G. Hawley ed., 9th ed., 1977); Concise Chemical and Technical Dictionary 1081 (H. Bennett ed., 4th ed., 1986); Hawley'S Condensed Chemical Dictionary 1186 (Richard J. Lewis, Sr. ed., 15th ed., 2007).*
Hawley'S Condensed Chemical Dictionary 753 (R.J. Lewis, Sr. ed., 15th ed., 2007).*
R.G. Pearson, Journal of the American Chemical Society, 85, 3533-3539 (1963).*
J. Leonard et al., Advanced Practical Organic Chemistry 129-226 (2nd ed., 1985).*
H. Diringer et al., Journal of Medicinal Chemistry, 13, 151-152 (1970).*
International Search Report, Form PCT/ISA/210, for corresponding PCT/EP2009/053271; date of mailing: Aug. 19, 2009.
English language Abstract for JP62000062.

* cited by examiner

*Primary Examiner* — James O Wilson
*Assistant Examiner* — Alexander R Pagano
(74) *Attorney, Agent, or Firm* — Michael P. Morris; Mary-Ellen M. Devlin

(57) ABSTRACT

The present invention relates to a method of making pyrimidines of formula (III), wherein X1, X2, R1 and R2 have the meanings as defined herein.

11 Claims, No Drawings

REGIOSELECTIVE PREPARATION OF SUBSTITUTED PYRIMIDINES

FIELD OF APPLICATION OF THE INVENTION

The present invention provides a new method for obtaining efficiently 2-amino-5-trifluoromethylpyrimidine derivatives which can be used as intermediates for the preparation of pharmacologically active compounds.

KNOWN TECHNICAL BACKGROUND

Aim of the Invention

In pyrimidine chemistry, for the majority of nucleophilic substitution reactions involving 2,4-functionalized pyrimidines and amines it is known that the first amine addition occurs preferentially (or exclusively) at the more reactive pyrimidine 4-position.

The reaction of pyrimidines of formula I' (where X is a leaving group; most commonly a halogen, particularly chlorine) and amines of formula II usually provides mixtures of regioisomers of formulae III' (2-amino pyrimidine derivatives) and IV' (4-amino pyrimidine derivatives) (see Scheme 1 below). Examples for such unselective reactions can be found in the art, inter alia, for the electron deficient 2,4-dichloro-5-trifluoromethylpyrimidine.

Scheme 1:

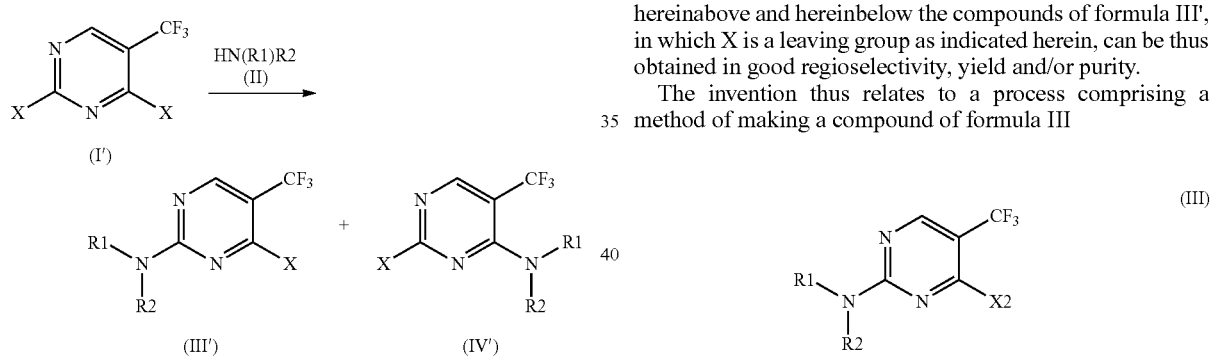

Thus, usually, the reactions of 2,4-dichloropyrimidine derivatives with amines provide non-selective mixtures of 2-chloro-4-amino-pyrimidines and isomeric 2-amino-4-chloropyrimidines in such that these reactions are of limited utility not only due to their lack of selectivity (and its impact on overall yield) but also because separation of the resulting isomers is generally extremely difficult and may require preparative HPLC, which is often not desired in a process sequence.

In contrast, there are only few examples where an amine is added to a 2,4-dichloropyrimidine in a selective manner to provide preferentially the 2-amino-4-chloropyrimidine. The most notable example of this type of reaction can be found in the international application WO 2005/023780 which describes a method for selective addition of an amine functionality to the C-2 position of a $CF_3$-substituted pyrimidine ring in the presence of a Lewis Acid (namely a salt of a metal ion) and a non-nucleophilic base.

However, there remains a need in the art for providing methods for obtaining efficiently compounds of formula III'. Further, there remains a need in the art for efficient providing compounds of formula III' vis-à-vis unselective regioisomeric mixtures. Further on, there remains a need in the art for efficient obtaining compounds of formula III' from unselective regioisomeric mixtures.

Other aims of the present invention will become apparent to the skilled man from the foregoing and following remarks.

DESCRIPTION OF THE INVENTION

It has now surprisingly been found, that by appropriate choice of the reaction solvent and further reaction particulars, one can preferentially add an amine functionality to the C-2 position of the pyrimidine ring via nucleophilic aromatic substitution reaction without needing the presence of any Lewis acidic metal ion.

Further, by reacting pyrimidine compounds of formula I', in which X is a leaving group, such as a halide, arylsulfonate, alkylsulfonate, perfluoroalkylsulfonate, arylsulfinate or alkylsulfinate, with amines of formula II in the presence of a non-nucleophilic auxiliary base using a non-nucleophilic alcohol (such as e.g. tert-butanol, tert-pentanol, neo-pentanol, sec-pentanol or sec-isoamylalcohol, or mixtures thereof) as reaction solvent at an appropriate reaction temperature one can obtain selectively compounds of formula III'. Advantageously, by the appropriate choice of the reaction conditions (e.g. reaction solvent and reaction temperature) one can achieve in this reaction that the desired regioisomer of formula III' directly precipitates from the reaction mixture and thus it can be easily separated off (whereas possible accompanying undesired isomers may remain in the mother liquor). Via the methods of the present invention described hereinabove and hereinbelow the compounds of formula III', in which X is a leaving group as indicated herein, can be thus obtained in good regioselectivity, yield and/or purity.

The invention thus relates to a process comprising a method of making a compound of formula III

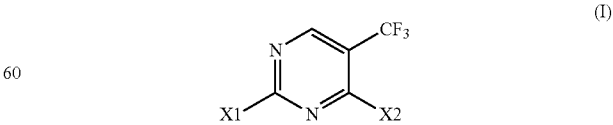

in which
X2 is a leaving group, such as
a halide, arylsulfonate, alkylsulfonate, perfluoroalkylsulfonate, arylsulfinate or alkylsulfinate; and
R1 and R2 are substituents independently selected from the group consisting of hydrogen, an aromatic group and an aliphatic group; or taken together and with inclusion of the nitrogen atom, to which they are attached, form a 4-11 membered aromatic or aliphatic ring; said method comprising reacting a compound of formula I (I)

with an amine of formula II [HN(R1)R2]
in the presence of a non-nucleophilic auxiliary base
in a solvent or mixture of solvents selected from non-nucleophilic alcohols to form a compound of formula III,
in which
X1 is a leaving group, such as a halide, arylsulfonate, alkylsulfonate, perfluoroalkylsulfonate, arylsulfinate or alkylsulfinate.

In a particular embodiment of this invention, X1 and X2 are the same or different and are each independently halides.

In a more particular embodiment of this invention, X1 and X2 are chloride.

A special aspect of the present invention is the abovementioned method characterized in that said reaction is performed as nucleophilic aromatic substitution reaction.

Another special aspect of the present invention is the abovementioned method characterized in that said reaction is performed without the presence of a Lewis acidic metal ion.

Another special aspect of the present invention is the abovementioned method characterized in that said reaction is for providing substantially (regio)isomerically pure or enriched compounds of formula III (such as e.g. better than 90:10, 95:5, 97:3, 99:1 or 99.5:0.5 in favour of the desired (regio)isomer).

Unless otherwise indicated, some terms used above and below to describe the compounds mentioned herein may be defined more closely as follows:

As used herein the term "aromatic", and specifically, an "aromatic group" refers to an aryl or heteroaryl radical as defined herein.

Further, an "aromatic amine" or "aromatic amine radical" refers to any amine or amine radical bound to at least one $sp^2$ carbon atom that is part of an aryl or heteroaryl group. An amine or amine radical will be referred to as an aromatic amine or radical even if the amine nitrogen is bound to a hydrogen or an $sp^3$ carbon atom, in addition to the one $sp^2$ carbon atom. Thus, for example, —HN($C_6$-$C_{10}$)aryl and —N(($C_1$-$C_6$)alkyl)(($C_6$-$C_{10}$)aryl) each refer to aromatic amine radicals as defined herein, despite the fact that each amine nitrogen is attached to non-aromatic substituents.

The term "aryl" refers to aromatic radicals such as phenyl, naphthyl, tetrahydronaphthyl, indanyl and the like. Unless otherwise mentioned, an "aryl" group may be optionally substituted with 1-3 suitable substituents, as defined herein. "Aryl" also refers to a phenyl radical fused to a non-aromatic heterocycle. Examples of such groups include but are not limited to 2-oxo-indolinyl, chromanyl, indolinyl and 2-oxo-3,4-dihydroquinolinyl optionally substituted by 1 to 3 suitable substituents.

As used herein, the term "heteroaryl" refers to an aromatic heterocyclic group usually with one heteroatom selected from O, S and N in the ring, wherein—unless otherwise mentioned—the aromatic heterocyclic group may be substituted by up to three suitable substituents as defined herein. In addition to said one heteroatom, the aromatic heterocyclic group may optionally have up to four N atoms in the ring. Examples of heteroaryl groups include but are not limited to pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents.

Alternatively, any ring carbon, —CH—, of the aforementioned heteroaryl group, may be replaced by a group selected from —C═O or —SO$_2$.

"Heteroaryl" also refers to one of the aforementioned heteroaryl groups fused to a non-aromatic heterocycle. Examples of such groups include but are not limited to 1,3-dihydro-pyrrolo[2,3-b]pyridin-2-one, 3,4-dihydro-1H-[1,8] naphthyridin-2-one, 1,3-dihydro-pyrrolo[2,3-b]pyridine and 3,4-dihydro-2H-pyrano[2,3-b]pyridine.

"Aliphatic", and specifically, an "aliphatic group" refers to an alkyl, cycloalkyl, or heterocycloalkyl radical, as defined herein. Aliphatic groups may be substituted with up to three suitable substituents as defined herein.

As used herein, the term "aliphatic amine" or "aliphatic amino radical" refers to any amine or amine radical in which the amine or radical nitrogen atom is bound to an $sp^3$ carbon that is part of an alkyl, cycloalkyl, or heterocycloalkyl group. Aliphatic amine groups may be substituted with up to three suitable substituents as defined herein.

The term "alkyl" refers to $C_1$-$C_{10}$ linear or branched alkyl groups (such as methyl, ethyl, n-propyl, isopropyl, n-butyl, isobutyl, sec-butyl, tert-butyl etc.), particularly $C_1$-$C_4$ alkyl, optionally substituted by 1 to 3 suitable substituents as defined herein.

The term "cycloalkyl" or "cyclyl" refers to $C_3$-$C_{12}$ mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonan), etc.) that is optionally substituted by 1 to 3 suitable substituents as defined herein. Bicyclic or tricyclic species may be fused, bridged or spirocyclic. Thus, examples of "cycloalkyl" or "cyclyl" groups, as defined herein, include, but are not limited to cyclopropyl, cyclobutyl, cyclopentyl, cyclohexyl, cycloheptyl, cyclohexenyl, bicyclo[2.2.1]heptanyl, bicyclo[3.2.1]octanyl, bicyclo[3.1.0]hexyl and spiro[2.4]heptyl.

The term "heterocycloalkyl" or "heterocyclyl" or "heterocycle" refers to a mono, bicyclic or tricyclic group containing 3 to 9 carbon atoms and 1 to 4 heteroatoms selected from —N, —NR, —O—, —S—, —SO— and —SO$_2$—, wherein—unless otherwise mentioned—the cyclic radical is optionally substituted by 1 to 3 suitable substituents as defined herein. Bicyclic or tricyclic species may be fused, bridged or spirocyclic. Examples of such groups include but are not limited to azetidinyl, pyrrolidinyl, piperidinyl, morpholinyl, piperazinyl, tetrahydrofuranyl, oxetanyl, thiomorpholinyl, quinuclidinyl, 5-aza-spiro[2.4]heptyl and 3-aza-bicyclo[3.1.0]hexyl.

As used herein, the term "halogen" includes fluoro, chloro, bromo or iodo or fluoride, chloride, bromide or iodide.

As used herein, the term "carbonyl" or "(C═O)" (as used in phrases such as alkylcarbonyl, alkyl-(C═O)— or alkoxycarbonyl) refers to the joinder of the >C═O moiety to a second moiety such as an alkyl or amino group (i.e. an amido group).

When two substituents attached to a nitrogen atom [such as in —N(R1)R2 or —N(R3)R4 or —N(R5)R6] taken together and with inclusion of the nitrogen atom, to which they are attached, form a cyclic amine, said amine can be a mono, bicyclic or tricyclic ring comprising 3 to 9 carbon atoms and 0 to 3 further heteroatoms selected from —N—, —O—, —S—, —SO— and —SO$_2$— (excluding the nitrogen atom to which the two substituents are attached).

The cyclic amine may be optionally substituted with 1 to 3 suitable substituents as defined herein. Bicyclic or tricyclic species may be fused bridged or spirocyclic. Examples of such cyclic amines include but are not limited to morpholine, azetidine, piperazine, piperidine, pyrrolidine, indoline, thiomorpholine.

A "suitable substituent" means a functional group which is suited for its intended function. Thus, said "suitable substituent" may mean a chemically and, if desired, pharmaceutically acceptable functional group. Such suitable substituents for the aforementioned aryl, heteroaryl, alkyl, cycloalkyl, heterocycloalkyl groups may be routinely described by those skilled in the art. Illustrative examples of said suitable substituents include, but are not limited to hydrogen, halo groups, perfluoroalkyl groups, perfluoroalkoxy groups, alkyl groups, alkenyl groups, alkynyl groups, hydroxy groups, oxo groups, alkylthio groups, arylthio groups, alkylsulfonyl groups, arylsulfonyl groups, heteroarylsulfonyl groups, alkylsulfonate groups, arylsulfonate groups, perfluoroalkylsulfonate groups, alkoxy groups, aryl or heteroaryl groups, cycloalkyl or heterocycloalkyl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups, dialkylaminocarbonyl groups, sulfonamido groups, alkylsulfonamido groups, dialkylsulfonamido groups, amido groups, N-acyl groups, arylcarbonyl groups, aryloxycarbonyl groups and the like, as well as, depending on the intended function, nitro, cyano and the like. Methylene groups may also be substituted for a carbonyl (C=O) group. Those skilled in the art will appreciate that many substituents can be substituted by additional substituents.

In general, if residues, substituents or groups occur several times in a compound they may have the same or different meanings.

The compounds and salts prepared by the methods of the present invention may exist in several isomeric forms. All isomeric forms (e.g. all stereoisomeric forms like chiral, enantiomeric, diastereomeric or racemic forms, atropisomeric, tautomeric and all geometric isomeric forms) of the compounds and salts thereof prepared by the methods of the present invention are intended within this invention, unless the specific isomer form is specifically indicated.

Thus, e.g. the compounds and salts prepared by the methods of the present invention may exist in several tautomeric forms, including the enol and imine form, and the keto and enamine form and geometric isomers and mixtures thereof. The preparation of all such tautomeric forms is included within the scope of the present invention. Tautomers exist as mixtures of a tautomeric set in solution. In solid form, usually one tautomer predominates. Even though the preparation of one tautomer may be described, the present invention encompasses the preparation of all tautomers of the present compounds.

The present invention also includes the preparation of atropisomers of the compounds prepared by methods of the present invention. Atropisomers refer to compounds that can be separated into rotationally restricted isomers.

The compounds prepared by the methods of the invention may contain olefin-like double bonds. When such bonds are present, the compounds exist as cis and trans configurations and as mixtures thereof and the present invention contemplates the preparation of such compounds.

As disclosed herein, compounds of formula III can be prepared by reaction of pyrimidine of formula I and a primary or secondary amine nucleophile of formula II in the presence of a non-nucleophilic auxiliary base in a suitable non-nucleophilic alcohol or mixture of non-nucleophilic alcohols as reaction solvent(s) at an appropriate reaction temperature, such as at room temperature, at elevated temperature or at the boiling temperature of the solvent(s) used. The meanings of X1 and X2 (which may be the same or different) on pyrimidine of formula I include those as described above, in particular X1 and X2 are the same or different and are each independently halides. Preferentially, X1 and X2 are the same and are chloride.

In an embodiment, the reaction partners are mixed by adding slowly the pyrimidine of formula I, preferably dissolved in a suitable solvent, to a solution of the amine of formula II and the auxiliary base in the reaction solvent(s).

Non-nucleophilic alcohols suitable as reaction solvents for the abovementioned reaction according to this invention include but are not limited to tert-butanol, tert-pentanol, neopentanol, sec-pentanol, sec-isoamylalcohol, or mixtures thereof. Preferentially, the abovementioned reaction is conducted in tert-butanol as reaction solvent.

Primary or secondary amine nucleophiles of formula II being useful in the abovementioned reaction according to this invention include those as described above. Particularly suitable amine nucleophiles of formula II for this reaction with compounds of formula I are primary aromatic amines (e.g. aniline derivatives) as described herein.

Non-nucleophilic auxiliary bases for use in the abovementioned reaction include, without being restricted thereto, inorganic and organic non-nucleophilic bases, such as e.g. inorganic carbonates (e.g. sodium carbonate, potassium carbonate, cesium carbonate or the like), tertiary amines (e.g. triethylamine, N,N-diisopropyl-ethyl-amine or the like) or other nitrogen bases, or alcoholates (e.g. potassium tert-butylate or the like), or the like. Preferentially, N,N-diisopropyl-ethyl-amine (DIPEA) is used as auxiliary base.

The reaction temperature for this reaction may range from about room temperature to about boiling temperature of the solvent(s) used. Particularly, the reaction is run at elevated temperature. Preferentially, tert-butanol is used as the sole reaction solvent and the reaction temperature may range from about 30° C. to about 80° C., more preferentially from about 40° C. to about 80° C.

For performing this reaction, it may be suitable to use—relative to the amount of the compound of formula I—a slight deficit of the amine of formula II (typically 0.9-1.0 equivalents) and/or a slight excess of the auxiliary base (typically 1.0-1.2 equivalents).

In a preferred embodiment of abovementioned method according to this invention, 2,4-dichloro-5-trifluoromethylpyrimidine is used as reactant which may be reacted with an aromatic amine, N,N-diisopropyl-ethyl-amine (DIPEA) is used as auxiliary base, and the reaction is run in tert-butanol as reaction solvent at elevated temperature, more specifically from about 40° C. to about 80° C., especially at about 80° C., to form the corresponding 2-amino-4-chloro-5-trifluoromethylpyrimidine derivative as major isomer.

The present invention also relates to processes disclosed herein, said processes may comprise methods of making and/or reacting compounds of formulae I, III and/or III' as described herein. The present invention also relates to the intermediates (including compounds of formula III or III'), including their salts, isomers and salts of these isomers.

Isolation and purification methods of the compounds obtained are known in the art and include, for example, removing the solvent(s), precipitation (e.g. with a co-solvent), crystallization, chromatography on a suitable support material (e.g. normal and reverse phase), extraction, trituration, and the like.

In a preferred embodiment, compounds of formula III obtained are isolated by precipitating it from the reaction mixture. Said precipitating may be performed as it is habitual for the skilled person, advantageously by crystallizing from the reaction mixture (especially when tert-butanol as reaction solvent is used), which may occur spontaneously from the hot reaction mixture or which may be induced by known methods (e.g. by adding seeding crystals and/or cooling) and which may be completed by cooling (e.g. to about 30° C.). For removing co-precipitated undesired salts from the precipitate, the precipitate may be suspended in water, stirred and filtered off. Finally, the product obtained may be washed with suitable solvents (such as e.g. tert-butanol and water) and dried.

Illustrative amines of formula II [HN(R1)R2] which may be used in the reaction according to this invention may include—without being restricted to—toluidine (e.g. 2- or 4-methylaniline), 5-amino-1,3-dihydro-indol-2-one, chloroaniline (e.g. 3- or 4-chloroaniline), methoxyaniline (e.g. 4-methoxyaniline or 2-methoxyaniline), (optionally substituted amino)-aniline (e.g. N-(4-aminophenyl)-amine), (optionally substituted aminocarbonyl)-aniline (e.g. N-{4-[R6 (R5)N—C(=O)]-phenyl}-amine where R5 and R6 are as defined herein), benzylamine, N-(4-methylbenzyl)-amine, N,N-dimethyl-1,4-phenylenediamine, cyclohexylamine, N-(cyclohexylmethyl)-amine, carboxyaniline (e.g. 4-carboxyaniline), piperidine, N-methyl-toluidine (e.g. N-methyl-p-toluidine), or the like.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 2007, 4rd Ed.) or in "Protecting Groups (Thieme Foundations Organic Chemistry Series N Group" by P. Kocienski (Thieme Medical Publishers, 2004).

In the reactions described herein, any reactive groups present such as carboxy-, carbonyl-, hydroxy-, amino-, alkylamino- or imino-groups may be protected during the reaction by conventional protecting groups which are cleaved again after the reaction.

For example, a protecting group for a carboxy group may be the methyl-, ethyl-, tert.-butyl- or benzyl-group, particularly the tert.-butyl-group.

For example, a protecting group for a carbonyl group may be an acetal or ketal like the 1,3-dioxolane- or the 1,3-dioxane-group.

For example, a protecting group for a hydroxy group may be a trimethylsilyl-, tert.-butyldimethylsilyl-, acetyl-, trityl-, benzyl- or tetrahydropyranyl-group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group, and additionally, for the amino group, a phthalyl group.

Thus, e.g., a suitably protected carboxyaniline within the meaning of this invention may be, for example, 4-amino-benzoic acid tert-butyl ester.

Thus, e.g., a suitably protected aminoaniline within the meaning of this invention may be, for example, (4-N-Boc-aminophenyl)-amine.

The cleavage of a carboxymethyl- or a carboxyethyl-group can for example be carried out hydrolytically in an aqueous solvent, e.g. in water, methanol/water, isopropanol/water, acetic acid/water, tetrahydrofuran/water or dioxane/water, in the presence of an acid such as trifluoroacetic acid, hydrochloric acid or sulphuric acid or in the presence of an alkali base as for example lithium hydroxide, sodium hydroxide or potassium hydroxide, but preferably sodium hydroxide, or aprotically in the presence of e.g. iodotrimethylsilane, at temperatures between 0 and 120° C., preferably at temperatures between 10 and 100° C.

An acetal or ketal can be cleaved with acetic acid, trifluoroacetic acid, hydrochloric acid, sulphuric acid or pyridiumium-p-toluene sulfonate in mixtures with water or in organic solvents like for example dichloromethane, 1,2-dichloroethane, tetrahydrofurane, dioxane, toluene or acetone at temperatures between −20° C. and 150° C., but preferably between 0° C. and 120° C.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetate, tetrahydrofurane, dioxane or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as dichloromethane, dioxane, methanol or diethylether.

For example, tert.butyl 4-(4-chloro-5-trifluoromethyl-pyrimidin-2-ylamino)-benzoate obtained by the method of this invention can be deprotected under acid conditions to yield 4-(4-chloro-5-trifluoromethyl-pyrimidin-2-ylamino)-benzoic acid. Corresponding procedures are described herein, e.g. such as described by way of example in the following examples.

A trimethylsilyl- or tert.-butyldimethylsilyl-group is cleaved with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, dioxane, acetonitrile or toluene at temperatures between −50° C. and 120° C., but preferably between −20° C. and 80° C.

A phthalyl group is preferably cleaved in the presence of hydrazine or a primary amine such as methylamine, ethylamine, ethanolamine or n-butylamine in a solvent such as methanol, ethanol, isopropanol, toluene/water or dioxane at temperatures between 20 and 50° C.

Amines of formula II or V can be provided as disclosed herein or they are known or can be obtained analogously or similarly to known procedures. Such as e.g. amines of formula V, e.g. cispentacin-isopropylamide, can be obtained as described in WO 2007/135036. In a particular embodiment the amines of formula II and V are both primary amines.

Compounds of formula I wherein both X1 and X2 are the same or different leaving groups independently selected from the group consisting of halide, arylsulfonate, alkylsulfonate, perfluoroalkylsulfonate, arylsulfinate and alkylsulfinate are known or can be obtained analogously or similarly to known procedures (e.g., a preparation of 2,4-dichloro-5-trifluoromethylpyrimidine is described in WO 2005/0123780).

Optionally, prior to further reaction, if the compounds of formula III obtainable via above reaction contain a functional group (e.g. —COOH), which may be temporarily protected by a suitable protecting group (e.g. by the benzyl protecting group as benzyloxycarbonyl or by the tertbutyl protecting group as tert-butyloxycarbonyl), the protecting group, if present, may subsequently be removed and the free functional group may be transformed to another functional group, such as e.g. the carboxyl group may be reacted with an primary or secondary amine of formula VI [HN(R5)R6] to give the amide group —CON(R5)R6, e.g. with the aid of a suitable coupling reagent for amide bond formation or via the respective carboxylic acid chloride, with or without isolation. In another embodiment, such conversion of a functional group may be performed later, e.g. on below-mentioned compounds of formula III' in which is X is —N(R3)R4, e.g. after the reaction described herein below.

Compounds of formula III, when reacted with an oxygen, sulfur or nitrogen nucleophile (such as e.g. with primary or secondary amines of formula V [HN(R3)R4] to provide 2,4-diamino products of formula III' in which X is —N(R3)R4), are useful intermediates in the preparation of pharmacological active compounds, such as e.g. protein kinase inhibitors which may be useful in the treatment of abnormal cell growth, such as cancer, in mammals. Compounds such as these are described, for example, in WO 03/030909, WO 03/032997, WO 03/078404, WO 2004/046118, WO 2004/048343, WO 2004/056807, WO 2004/056786, WO 2005/026130, WO 2005/049033, WO 2005/111023, WO 2005/113515, WO2006/021544, US 2006/025433, WO 2006/074057, WO 2006/091737, WO 2006/099974, WO 2006/117560, WO 2007/003596, WO 2007/049041, WO 2007/063384, WO 2007/072158, WO 2007/096351, WO 2007/115999, US 2007/203161, WO 2007/132010, WO 2007/140957, WO 2008/003766, and WO2008/129380.

Amines of formula V or VI are primary or secondary amines, in which R3 and R4 or, respectively, R5 and R6 are substituents independently selected from the group consisting of hydrogen, an aromatic group and an aliphatic group; or R3 and R4 or, respectively, R5 and R6 taken together and with inclusion of the nitrogen atom to which they are attached form a 4-11 membered aromatic or aliphatic ring. Amines of formula V or VI include, without being limited to, cyclic amines or primary or secondary aliphatic amines, such as e.g. those mentioned herein, e.g. those wherein one of R3 and R4 or of R5 and R6, respectively, is hydrogen or alkyl and the other is optionally substituted alkyl, cycloalkyl or heterocycloalkyl as described herein, such as e.g. N-alkyl-amines, N-cycloalkyl-amines, N-heterocycloalkyl-amines, N-alkyl-N-methyl-amines, N-cycloalkyl-N-methyl-amines or N-heterocycloalkyl-N-methyl-amines, each alkyl, cycloalkyl or heterocycloalkyl optionally substituted as defined herein. Examples of amines of formula V include, without being limited, cyclopropylamine, cyclobutylamine, cyclopentylamine, cyclohexylamine, (1S,2R)-2-amino-1-cyclopentane carboxylic acid or its amide or isopropylamide, (1S,2R)-2-amino-cyclohexyl-carbamic acid benzyl ester or -carbamic acid tert.butyl ester, and the like. Examples of amines of formula VI include, without being limited, (1-methyl-piperidin-4-yl)-amine, (1-Boc-piperidin-4-yl)-amine, (1-methyl-piperidin-4-yl)-methyl-amine, (1-Boc-piperidin-4-yl)-methyl-amine, piperidine, morpholine, N-Boc-piperazine, N-methyl-piperazine, homopiperidine, N-methyl-homopiperazine, N-Boc-homopiperazine, and the like. The Boc or Cbz protecting group may be removed after the reaction to yield the free amine.

It is to be understood, that certain compounds of formula III or III' as defined herein can be converted into other compounds of formula III or III', respectively, via synthesis strategies and reactions customary to the skilled person, such as e.g. comprising one or more of the methods a) to h) mentioned below.

Therefore, optionally, for example, from compounds of formula III or III' as defined herein a) which contains a carboxyl group, the corresponding ester compounds can be obtained via esterification reaction, and/or the corresponding amide compounds can be obtained by acidification reaction;

b) which contains an ester group, the corresponding free acid compounds can be obtained via de-esterification reaction (e.g. saponification);

c) which contains a primary or secondary amino group, the corresponding amides can be obtained via acylation reaction, and/or the corresponding sulfonamides can be obtained via sulfonylation reaction;

d) which contains a hydroxyl group, the corresponding esters can be obtained via acylation reaction;

e) which contains an acylated hydroxyl group and/or an acylated amino group, the corresponding free alcohols and/or free amines can be obtained via de-acylation reaction;

f) which contains a primary or secondary amino group and/or a hydroxyl group the corresponding N-alkylated and/or O-alkylated compounds, respectively, can be obtained via N-alkylation and/or O-alkylation reaction, respectively;

g) which contains a replaceable leaving group, its replacement yielding the corresponding substituted compounds can be obtained via nucleophilic substitution reaction with N, O or S nucleophiles; and/or h) which contains an oxidizable nitrogen or sulphur atom (e.g. aromatic or aliphatic heterocycles containing an amino- or imino-type ring nitrogen or sulphur atom), the corresponding N-oxides and/or S-oxides (including mono- and di-oxides), respectively, can via obtained by N- and/or S-oxidation reaction, respectively.

The methods mentioned under a) to h) can be expediently carried out analogously to the methods known to the person skilled in the art or as described by way of example herein.

Finally, optionally, the trifluoromethyl group of 2,4-diamino pyrimidine derivatives of formula III' in which X is —N(R3)R4 as defined herein may be hydrolyzed to form the corresponding acids, and, optionally, the thus obtained acids may be subsequently decarboxylated to form the corresponding des-trifluoromethyl derivatives. Corresponding methods are known to the skilled person.

The compounds or intermediates obtained can be further reacted without isolation or in situ, or they can be isolated and purified in a manner known per se, e.g. as described herein, for example by removing or distilling off the solvent under reduced pressure or by precipitating (e.g. by concentrating the solution, cooling and/or adding a nonsolvent), collecting, and, optionally, recrystallizing the residue obtained from one, two or more suitable organic or aqueous solvents (such as e.g. selected from those solvents mentioned below), or subjecting it to one of the customary purification methods, such as, for example, column chromatography on a suitable support material.

Unless otherwise noted herein, in general but depending upon the specific requirements, appropriate solvents for the procedures mentioned herein may be selected from the group consisting of low-molecular-weight aliphatic alcohols, such as methanol, ethanol, propanol or isopropanol; esters, such as ethyl acetate; ketones, such as acetone, methyl ethyl ketone or methyl isobutyl ketone; ethers, such as diethyl ether, diisopropyl ether, tetrahydrofuran or dioxane; optionally chlorinated hydrocarbons, such as n-hexane, petrolether, toluene, methylene chloride or chloroform; amides or lactames such as e.g. N,N-dimethylformamide or N-methyl-2-pyrrolidone, and nitriles such as e.g. acetonitrile, or the like, or a mixture of solvents, with or without water, or water alone.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following example. The following example serve to illustrate, by way of example, the principles of the invention without restricting it.

EXAMPLES

Method According to the Invention a.) A suspension of 71.3 g (552.0 mmol) diisopropyl ethyl amine and 88.9 g (460.0 mmol) of 4-amino-benzoic acid tert-butyl ester in 620 mL tert.-butanol is warmed to 80° C. To the obtained solution a solution of 104.8 g (483.0 mmol) 2,4-dichloro-5-trifluoromethylpyrimidine in 270 mL tert.-butanol is added slowly in 1 hour. The obtained suspension is stirred for 4 hours at 80° C. The suspension is cooled to 30° C. and 180 mL of purified water is added. The suspension is stirred for 30 minutes at 30° C. The precipitate is filtered and washed twice with 170 mL of warm tert.-butanol (30° C.) and with 355 mL of purified water. The product is dried at 50° C. As product 103 g (60%) of the desired 2-amino pyrimidine derivative is obtained as slightly yellowish solid with 99.6% purity (HPLC).

$^1$H-NMR (400 MHz) (DMSO-d$_6$): δ (ppm)=10.99 (bs, 1H); 8.88 (s, 1H) 7.99-7.74 (m, 4H); 1.53 (s, 3H) HPLC ret. Time: 11.135 min.

MS: M+H$^+$=374/6

Analytical HPLC chromatography and conditions:

Manufacturer: Phenomenex; Column: Synergi Max-Max-RP; Dimention: 150×4.6 mm, Mobile phase: A: 0.3% KH2PO4/pH=4.7. B: Acetonitrile; Gradient: from B (50%) to B (70%) in 8 min. hold for 15 min. at B (70%); Flow rate: 1.5 mL/min.; Detection: UV 200 nm; Temperature: 40° C.; Injection vol.; 2 μL b.) Optionally in a subsequent step, a mixture of the 2-amino-pyrimidine derivate of formula III obtained in step a) as described above, i.e. 4-(4-chloro-5-trifluoromethyl-pyrimidin-2-ylamino)-benzoic acid tert.butyl ester (50.0 g; 133.8 mmol), acetonitrile (420 ml) and thionyl chloride (31.8 g; 267.6 mmol) is warmed to 70° C. Purified water (4.82 g; 267.6 mmol) is added slowly. The reaction mixture is warmed for 1 hour at 70° C. After cooling to 2° C. the precipitate is filtered and washed with acetonitrile (200 ml). The product is dried at 40° C. As product 39.9 g (89.8%) of the corresponding acid chloride derivative, i.e. 4-(4-chloro-5-trifluoromethyl-pyrimidin-2-ylamino)-benzoylchloride, is obtained as slightly yellowish crystals.

$^1$H-NMR (400 MHz) (CDCl$_3$): δ (ppm)=8.67 (s, 1H); 8.15 (d, 2H, J=8 Hz); 7.81 (d, 2H, J=8 Hz); 7.73 (bs, 1H).

In an alternative variant of step b), the corresponding free acid can be isolated as follows: A mixture of 2-amino-pyrimidine derivate of formula III obtained in step a) as described above (10.0 g; 26.8 mmol) and acetonitrile (70 ml) is warmed to 70° C. and a solution of thionyl chloride (29.4 mmol) in acetonitrile (30 ml) is added. The reaction mixture is stirred for 1 hour. After cooling to 10° C. purified water (50 ml) is added, the precipitate is filtered and washed with cold acetonitrile. The product is dried at 50° C. As product 8.5 g (97.5%) of the corresponding acid, i.e. 4-(4-chloro-5-trifluoromethyl-pyrimidin-2-ylamino)-benzoic acid, is obtained as white powder.

$^1$H-NMR (400 MHz) (DMSO-d$_6$): δ (ppm)=12.67 (bs, 1H); 10.99 (s, 1H); 8.90 (s, 1H); 7.94 (d, 2H, J=8 Hz); 7.85 (d, 2H, J=8 Hz).

c) In a further optional step, to a cold suspension or solution of the above-obtained acid chloride derivative of step b) (e.g. 1.7 eq) in a suitable solvent (e.g. acetonitrile), which may further comprises a suitable inorganic or organic auxiliary base (e.g. N,N-diisopropylethylamine, e.g. 1.4 eq), an appropriate amine of formula VI (e.g. 1.0 eq) is added. The solution or suspension is stirred and purified water is added. The cold suspension is filtered (e.g. at about 10° C.) and the collected precipitate is washed with a cold mixture of solvent/water (e.g. acetonitrile and purified water). The product may be dried at reduced pressure and/or elevated temperature (e.g. about 50° C.). As product the corresponding amide derivative is obtained.

d) In a yet further optional step, the above amide derivative of step c) (e.g. 1.0 eq) and an appropriate amine of formula V (e.g. 1.2 eq) are suspended or dissolved in a suitable solvent (e.g. a lower aliphatic alcohol such as methanol, ethanol or isopropanol). A suitable inorganic or organic auxiliary base (e.g. N,N-diisopropylethylamine, e.g. 1.1 eq) is added and the reaction mixture is warmed (e.g. to about 80° C.). The reaction solvent is largely removed and the residue partitioned in an organic-aqueous biphasic system (e.g. with a suitable ether, ester, ketone, haloalkane or the like as organic solvent) optionally comprising a suitable inorganic or organic base (e.g. an aqueous sodium carbonate or sodium hydrogen carbonate solution). After phase separation, the organic solvent is removed and the residue optionally further purified. The corresponding 2,4-diamino pyrimidine derivative is obtained as product.

In an optional alternative, the initially obtained compound of step a) can be reacted with an appropriate amine of formula V analogously or similarly as described in step d) to give the corresponding 2,4-diamino pyrimidine derivative, which can be then optionally further reacted analogously or similarly as described in step b) and c).

The invention claimed is:

1. A method for making 4-(4-chloro-5-trifluoromethyl-pyrimidin-2-ylamino)-benzoic acid tert.butyl ester having the formula

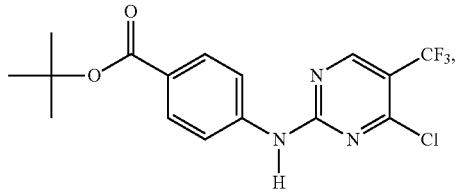

comprising reacting 2,4-dichloro-5-trifluoromethylpyrimidine having the formula

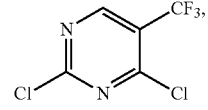

with 4-amino-benzoic acid tert-butyl ester having the formula

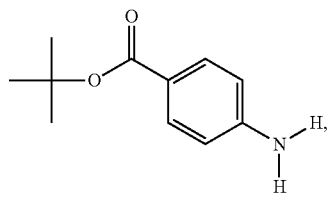

in the presence of a non-nucleophilic auxiliary base which is N,N-diisopropyl-ethylamine, in a solvent or mixture of solvents selected from non-nucleophilic alcohols to form 4-(4-chloro-5-trifluoromethyl-pyrimidin-2-ylamino)-benzoic acid tert.butyl ester having the formula

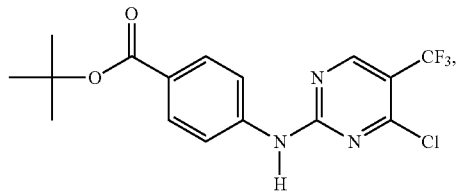

characterized in that said reaction is conducted without any Lewis acidic metal cation.

2. The method of claim 1 wherein said non-nucleophilic alcohols are tert-butanol, tert-pentanol, neo-pentanol, sec-pentanol and sec-isoamylalcohol.

3. The method of claim 1 wherein said non-nucleophilic is tert-butanol.

4. The method of claim 1 wherein said reaction is conducted at a reaction temperature from about room temperature to about boiling temperature of the solvent(s) used.

5. The method of claim 1 wherein said reaction is conducted at a reaction temperature from about 40° C. to about 80° C.

6. The method of claim 1 wherein said reaction is conducted at about 80° C.

7. The method of claim 1 further comprising the steps of precipitating 4-(4-chloro-5-trifluoromethyl-pyrimidin-2-ylamino)-benzoic acid tert.butyl ester from the reaction mixture, collecting the precipitate, washing the precipitate and drying the precipitate.

8. The method of claim 1 further comprising the step of reacting said 4-(4-chloro-5-trifluoromethyl-pyrimidin-2-ylamino)-benzoic acid tert.butyl ester with an oxygen, sulphur or nitrogen nucleophile.

9. The method of claim 7 further comprising suspending the precipitate in water after it is precipitated from the reaction mixture.

10. The method of claim 7 characterized in that the precipitate is a substantially regioisomerically pure (90:10 or higher) 4-(4-chloro-5-trifluoromethyl-pyrimidin-2-ylamino)-benzoic acid tert.butyl ester.

11. The method of claim 1 characterized in that a substantially regioisomerically pure (90:10 or higher) 4-(4-chloro-5-trifluoromethyl-pyrimidin-2-ylamino)-benzoic acid tert.butyl ester is produced.

* * * * *